US012782309B2

(12) United States Patent
Murphy

(10) Patent No.: US 12,782,309 B2
(45) Date of Patent: Nov. 3, 2026

(54) BIODIESEL FLUID SENSOR

(71) Applicant: SSI Technologies, LLC, Janesville, WI (US)

(72) Inventor: Gregory P. Murphy, Midland City, AL (US)

(73) Assignee: SSI Technologies, LLC, Janesville, WI (US)

( * ) Notice: Subject to any disclaimer, the term of this patent is extended or adjusted under 35 U.S.C. 154(b) by 150 days.

(21) Appl. No.: 19/030,583

(22) Filed: Jan. 17, 2025

(65) Prior Publication Data

US 2026/0338726 A1 Oct. 29, 2026

(51) Int. Cl.

| | |
|---|---|
| ***G01N 27/22*** | (2006.01) |
| ***G01F 23/263*** | (2022.01) |
| *G01N 29/024* | (2006.01) |
| *G01N 33/22* | (2006.01) |

(52) U.S. Cl.

CPC ......... *G01N 27/221* (2013.01); *G01F 23/265* (2013.01); *G01N 27/223* (2013.01); *G01N 29/024* (2013.01); *G01N 33/22* (2013.01); *G01N 2291/011* (2013.01); *G01N 2291/02433* (2013.01); *G01N 2291/02809* (2013.01)

(58) Field of Classification Search

CPC ... G01N 2015/1486; G01N 2015/0053; G01N 15/1459; G01N 2015/1006; G01N 27/221; G01N 27/223; B01D 46/0036; B01D 46/30; B01D 46/62; G01F 23/2962; G01F 23/265

See application file for complete search history.

(56) References Cited

U.S. PATENT DOCUMENTS

| | | | | |
|---|---|---|---|---|
| 5,265,460 | A | 11/1993 | Ellinger et al. | |
| 7,406,871 | B2 | 8/2008 | Sugiura | |
| 8,264,243 | B2 | 9/2012 | Tarui et al. | |
| 9,377,441 | B2 * | 6/2016 | Reimer | G01N 29/024 |
| 9,488,514 | B2 | 11/2016 | Murphy | |
| 9,910,025 | B2 * | 3/2018 | Kumar | G01F 23/2921 |
| 9,953,038 | B2 | 4/2018 | Testardi | |
| 10,151,730 | B2 | 12/2018 | Reitmeier et al. | |
| 10,571,431 | B2 * | 2/2020 | Reimer | G01N 29/024 |
| 2021/0247340 | A1 | 8/2021 | Meyer et al. | |

OTHER PUBLICATIONS

French Patent Office Action for Application No. 2600582 dated Mar. 23, 2026 (4 pages including English machine translation).

Campo et al., "An Ultrasonic-Capacitive System for Online Characterization of Fuel Oils in Thermal Power Plants", Sensors, 2021; 21(23):7979, https://doi.org/10.3390/s21237979 (25 pages).

* cited by examiner

*Primary Examiner* — Vinh P Nguyen

(74) *Attorney, Agent, or Firm* — Michael Best & Friedrich LLP

(57) ABSTRACT

A fluid sensor that in some instances includes a target; a temperature sensor; a transducer positioned opposite the target at a fixed, predetermined distance from the target and configured to generate an ultrasonic sound, receive an echo of the ultrasonic sound, and output a signal based on the echo; a sensing area located between the transducer and the target; a capacitor; and an electronic processor electrically connected to the temperature sensor, the transducer, and to the capacitor and configured to determine a percentage of each of two or more constituent components of the fluid based on the speed of sound, the capacitance, and a system of equations.

23 Claims, 11 Drawing Sheets

| Fuel | Density (g/ml) | Viscosity ($mm^2/s$) | Dielectric Constant |
|---|---|---|---|
| #2 Diesel | 0.85 | 4.5 | 2.3 |
| Kerosene | 0.78 | 2 | 2 |
| FAME | 0.88 | 4.5 | 3.9 |
| HVO | 0.78 | 3 | 2.1 |

FIG. 7

BIODIESEL FLUID SENSOR

BACKGROUND

Fluid level and fluid quality sensing is useful in several vehicle applications. Knowing the level or amount of a fluid (for example, fuel) is important so that the fluid can be replenished before it is consumed entirely. Knowing the quality of a fluid can help determine the type of fluid within a tank or other container. If a sensor provides this information or information that is indicative of quality, then a computer or similar device can determine whether the correct fluid has been introduced into the tank. In vehicles with diesel engines, sensing of diesel exhaust fluid (DEF) is important to ensure proper functioning of selective catalytic reluctant (SCR) diesel emission-control systems. Selective catalytic reduction (SCR) is a method of converting oxides of nitrogen (NOx) created during the combustion of diesel fuel into diatomic benign nitrogen gas ($N_2$) and water ($H_2O$) by a catalytic reaction. DEF is used in the SCR process. When an SCR exhaust treatment system is used in a diesel-powered vehicle, the emission of NOx is significantly reduced.

SUMMARY

While sensing quantity (for example, level) and quality (for example, concentration) is in important with respect to DEF used in SCR systems, in other vehicle applications it may also be important to sense the quantity and/or quality of other fluids. Biodiesel is a fluid of interest because it is a renewable and biodegradable fuel. Numerous countries in Europe and North America have established regulations, and in some cases have incentives, regarding biodiesel use. Regulations and incentives have been put in place because, among other things, biodiesels are known to reduce pollutants except for NOx. However, burning biodiesels in diesel engines configured to burn petroleum diesel (or, simply "diesel") can lead to increased NOx output. In some cases, use of biodiesel in engines tuned to burn diesel can increase NOx emissions by 4 to 10 percent. Therefore, there is a need for a fluid sensor configured to measure the percentage of biodiesel in a tank so that modifications may be made to the ignition timing and amount of DEF injected in an SCR exhaust treatment system to allow the engine to meet NOx emissions requirements.

In many instances, diesel fuel from a standard diesel fuel pump is a combination of diesel (refined from petroleum), kerosene (refined from petroleum), and biodiesel. The ratios of these components as constituents of the diesel fuel vary due to several factors. For example, Europe has seven different standard mixtures depending on region. The United States allows fuel distributors to control the diesel fuel blends for various regions depending on temperatures in the regions.

Some diesel fuels contain biodiesel that varies depending on which fats are used as a base for the fuel. Biodiesel is typically made by combining vegetable oil, methanol, and lye at 60 degrees Celsius. However, there are other types of biodiesels. Hydrogenated vegetable oil (HVO) is one type of biodiesel that is made by reacting hydrogen gas with vegetable oil. Fatty acid methyl ester (FAME) is another type of biodiesel. Physical and chemical properties vary between types of biodiesels. For example, HVO has a lower freezing point (−40 degrees Celsius) than FAME, which has a freezing point of −5 degrees Celsius. As an aside, because HVO has a relatively low freezing point, fuels with HVO have a relatively lower freezing point.

The distinct chemical and physical properties of different biodiesels make them more advantageous to use in different regions. This leads to the availability of many different types of diesel fuel. Since various diesel fuel mixtures are available, there is a need for determining percentages of diesel, kerosene, and biodiesel within diesel fuel to, among other things, determine the NOx emissions of the diesel fuel mixtures and ensure that the NOx levels abide by legislative thresholds.

Although physical properties can differ in different types of biodiesels, in some instances some of the properties are the same. Therefore, there is a need for selecting a group of physical properties of biodiesels that can distinguish biodiesels. In addition, diesel and kerosene have similar physical properties with one another and, in some instances, with biodiesels. For example, the physical properties of HVO and kerosene are nearly the same. Therefore, diesel fuels with kerosene as a constituent component are less susceptible to freezing or freeze at a lower temperature. For this reason, diesel fuels usually contain either kerosene or HVO as an anti-freeze agent. Additionally, because the physical properties of kerosene and HVO are nearly identical, there is no need to measure and differentiate between the two. The similarity in characteristics of these fluids increases the importance of selecting the right group of physical characteristics to distinguish between different types of biodiesels. For example, FAME has a significantly higher dielectric constant that diesel and kerosene. Therefore, determining the percentage of FAME in a fluid can be accomplished using information regarding the dielectric constant, assuming there is no need to distinguish the percentages of diesel and kerosene in a fluid. Although calculating a speed of sound though a fluid can provide more information on amounts of diesel and kerosene in the fluid is helpful, it is not sufficient when determining the presence of FAME or other biodiesel concentrations in the fluid. Therefore, there is a need for a fluid sensor or sensing system that incorporates both the capacitance and the speed of sound of a fluid for determining percentages of diesel, kerosene, and biodiesel in a fluid. Thus, some examples of fluid sensors disclosed herein are configured to sense the capacitance of the fluid and the speed of sound though the fluid.

Accordingly, one example provides, a fluid sensor that includes a target; a transducer positioned opposite the target at a fixed, predetermined distance from the target and configured to generate an ultrasonic sound, receive an echo of the ultrasonic sound, and output a signal based on the echo; a sensing area located between the transducer and the target; a capacitor; and an electronic processor electrically connected to the transducer and to the capacitor and configured to determine a speed of sound of a fluid based on the signal from the transducer; determine a capacitance of the fluid based on a signal from the capacitor; and determine a percentage of each of two or more constituent components of the fluid based on the speed of sound, the capacitance, and a relationship in which a sum of the percentages of the two or more constituent components equals one hundred.

Another example provides a method for operating a fluid sensor. In one instance the method includes generating, via a transducer, an ultrasonic sound; receiving an echo of the ultrasonic sound, and outputting, via an electronic processor, a signal based on the echo; determining, via the electronic processor, a speed of sound of a fluid based on the signal from a transducer; determining, via the electronic processor, a capacitance of the fluid based on a signal from a capacitor;

and determining, via the electronic processor, a percentage of each of two or more constituent components of the fluid based on the speed of sound, the capacitance, and a system of equations, that in one instance includes a relationship in which a sum of the percentages of the two or more constituent components equals one hundred.

In some instances, sensors disclosed herein include a filter or similar feature to help address adverse consequences of aeration. Biodiesel and other fluids can become aerated (i.e., mixed with air in such a way that bubbles of air are entrained in the fluid). Aeration can occur, for example, during rapid filling or refilling of a tank or reservoir for fluid. Aeration can also occur during vehicle vibration, fluid sloshing within the tank, or may be present in the return flow of fluid if a pump of the system ingests air.

Generally, accurate fluid measurements require a fluid that has little to no aeration. When the fluid is aerated the path of the ultrasonic sound waves are dispersed by the presence of air bubbles. Interference of the sound waves causes a loss in the reflected echo (i.e., no speed of sound measurement) and thus a loss of accurate fluid measurements.

Other embodiments, examples, aspects, and features will become apparent by consideration of the detailed description and accompanying drawings.

BRIEF DESCRIPTION OF THE DRAWINGS

FIG. 7 is a table of example types of fluid and the corresponding physical properties of the fluid types.

DETAILED DESCRIPTION

Before any embodiments, examples, aspects, or features are explained in detail, it is to be understood that the embodiments, examples, aspects, or features are not limited to the details of construction and the arrangement of components set forth in the following description or illustrated in the following drawings. Other embodiments, examples, aspects, and features are possible and capable of being practiced or of being carried out in various ways.

For ease of description, some or all the example systems presented herein are illustrated with a single exemplar of each of its component parts. Some examples may not describe or illustrate all components of the systems. Other examples may include more or fewer of each of the illustrated components, may combine some components, or may include additional or alternative components.

Unless the context of their usage unambiguously indicates otherwise, the articles "a," "an," and "the" should not be interpreted as meaning "one" or "only one." Rather these articles should be interpreted as meaning "at least one" or "one or more." Likewise, when the terms "the" or "said" are used to refer to a noun previously introduced by the indefinite article "a" or "an," "the" and "said" mean "at least one" or "one or more" unless the usage unambiguously indicates otherwise.

It should also be understood that although certain drawings illustrate hardware and software located within particular devices, these depictions are for illustrative purposes only. In some implementations, the illustrated components may be combined or divided into separate software, firmware and/or hardware. For example, instead of being located within and performed by a single electronic processor, logic and processing may be distributed among multiple electronic processors. Regardless of how they are combined or divided, hardware and software components may be located on the same computing device or may be distributed among different computing devices connected by one or more networks or other suitable communication links.

Thus, in the claims, if an apparatus or system is claimed, for example, as including an electronic processor or other element configured in a certain manner, for example, to make multiple determinations, the claim or claim element should be interpreted as meaning one or more electronic processors (or other element) where any one of the one or more electronic processors (or other element) is configured as claimed, for example, to make some or all of the multiple determinations. To reiterate, those electronic processors and processing may be distributed.

Figure 1:
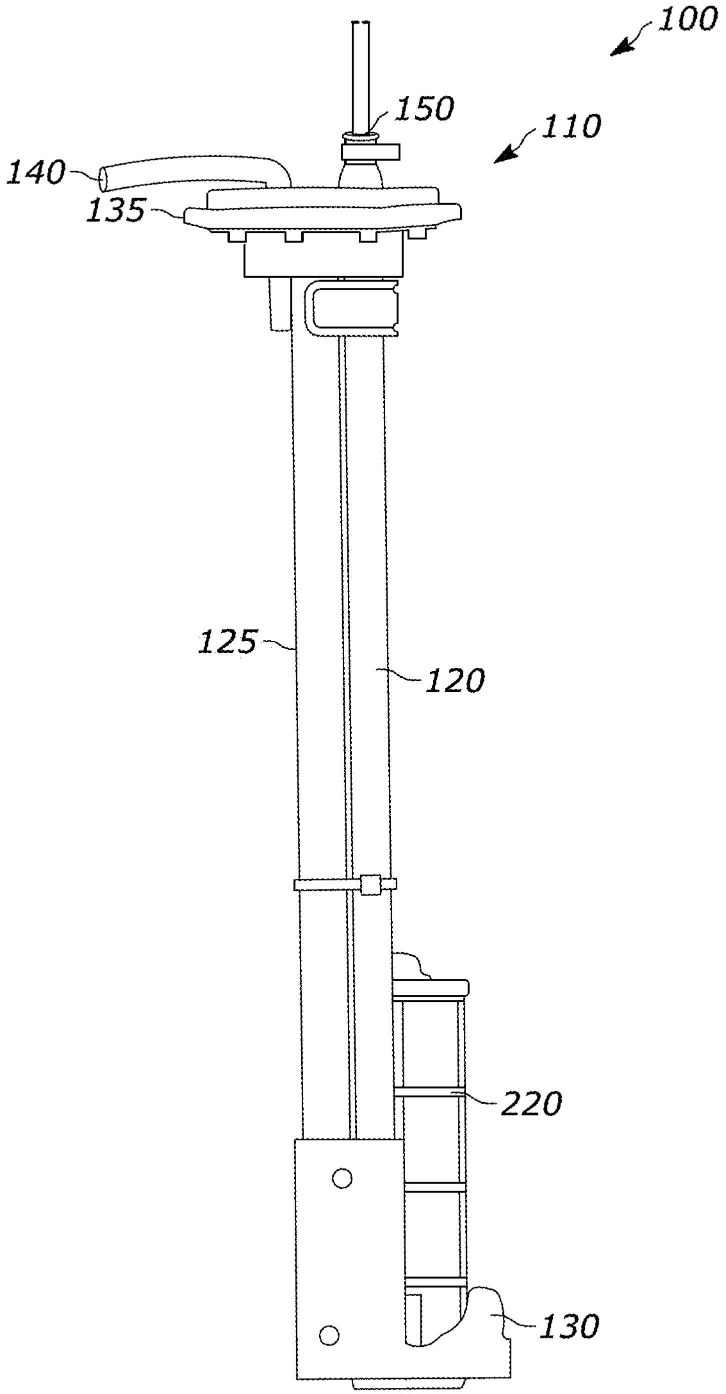
FIG. 1 is a side view of a fluid sensor or sensing system, according to some examples.
Figure 2:
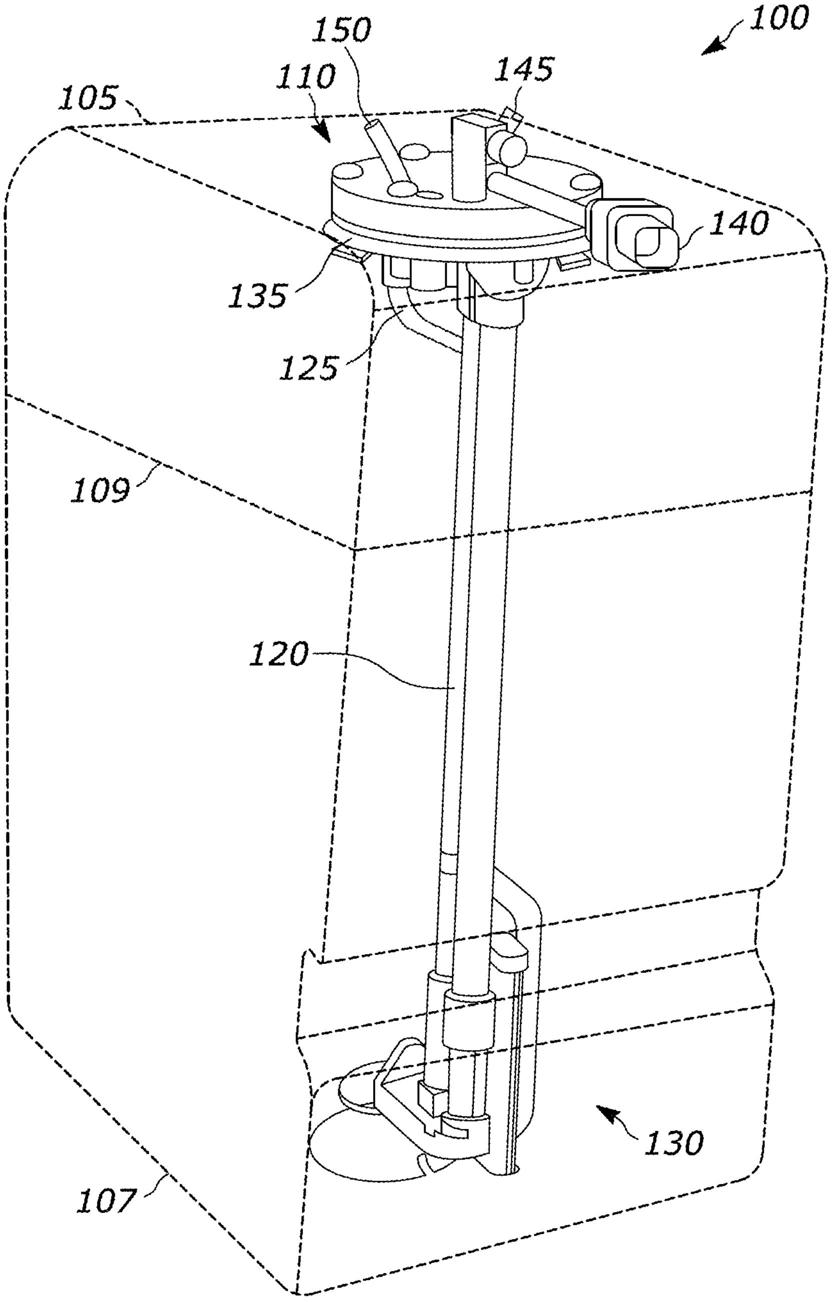
FIG. 2 is a perspective view of a fluid sensor in a tank that holds a fluid, according to some examples.

FIGS. 1 and 2 illustrate an example of a fluid sensor 100 for sensing a fluid. In FIG. 2 the sensor 100 is shown mounted in a tank 105 that holds a fluid, for example, biodiesel. The fluid sensor 100 includes multiple components and at least one sensing system. In the example shown, the fluid sensor 100 includes a sensing system 130. Descriptions of various components and aspects of the sensor 100 illustrated in FIGS. 1 and 2 are provided later.

Figure 3A:
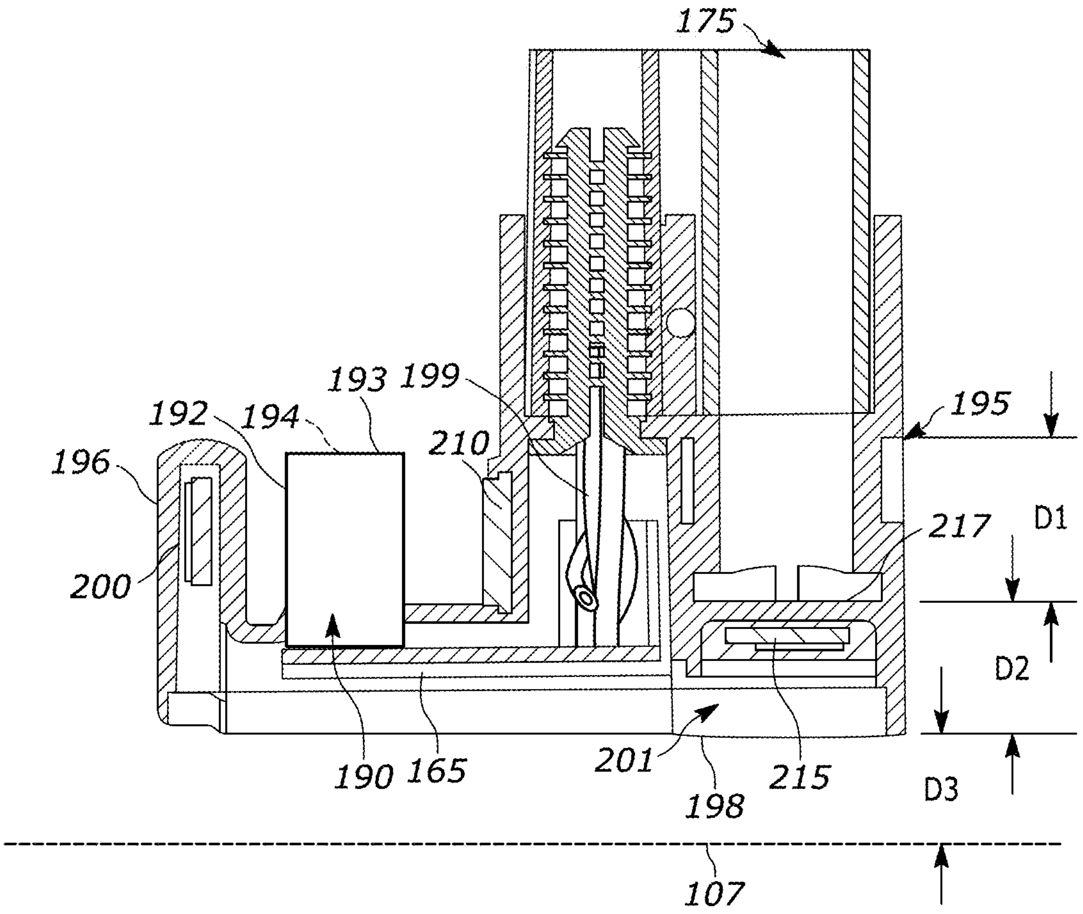
FIG. 3A is a sectional view of a fluid sensor or sensing system, according to some examples.
Figure 3B:
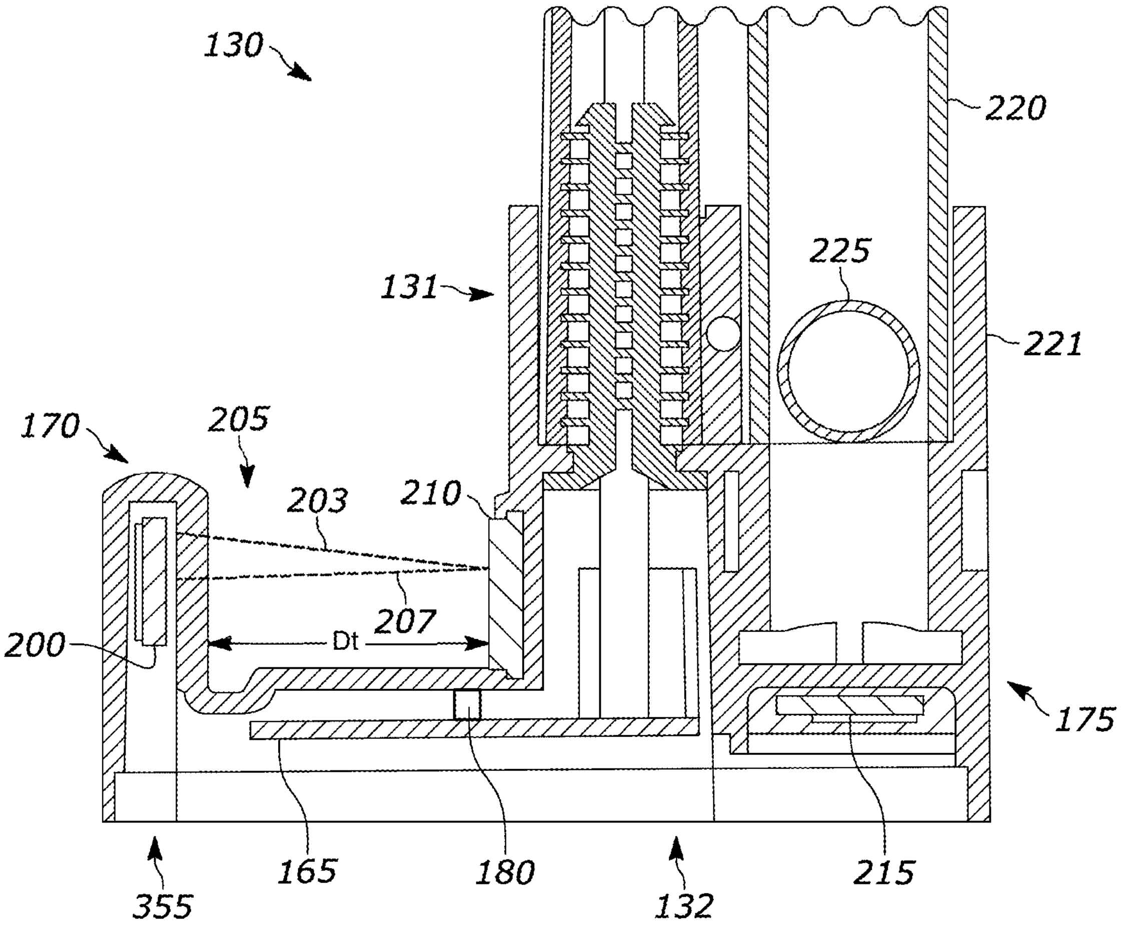
FIG. 3B is a sectional view of a fluid sensor or sensing system, according to some other examples.

FIGS. 3A-3B illustrate a sectional view of the sensing system 130. In the example shown, the sensing system 130 includes a top 131 and a bottom 132. In the example shown, the sensing system 130 is a component of the fluid sensor 100 and the sensing system 130 includes components that by themselves may be considered sensors. In the example shown, the sensing system 130 includes a printed circuit board (PCB) 165 (on which one or more components shown in FIG. 4A may be mounted) and a plurality of sensors. In the example shown, the plurality of sensors includes an ultrasonic sensor 170, a level sensor 175, a temperature sensor 180, and a capacitance sensor or capacitor 190. In other examples, the sensing system 130 may include more or fewer sensors than shown. In one example, each of the plurality of sensors is electrically coupled to the PCB 165. In some examples, the PCB 165 includes a sensor control system, for example, the sensor control system illustrated in FIG. 4A, which, among other things and in only one example, provides power to the plurality of sensors; analyzes signals from the plurality of sensors; and outputs the determinations to other components such as an external computer.

The ultrasonic sensor 170 includes a transducer (referred to in some instances as a concentration transducer 200) that generates ultrasonic sound 203 in response to an electric signal and outputs an electric signal in response to receiving a sound, for example, an echo 207 of the ultrasonic sound 203 that the concentration transducer 200 generates. In the example shown, the ultrasonic sensor 170 outputs a signal that is representative of the speed of sound of the fluid contained within the tank in which the sensor 100 is located. Since the speed of sound in a fluid is correlated to the concentration of the fluid at a specific temperature, the ultrasonic sensor 170 may also be referred to as a concentration sensor 170. Concentration is an aspect of the quality of a fluid and, thus, the concentration sensor 170 provides information regarding the quality of a fluid. In the example shown, the concentration sensor 170 includes the concentration transducer 200, a measurement channel or sensing area 205, and a target 210. The concentration transducer 200 is positioned at a fixed, predetermined distance Dt from the target 210. In some instances, the concentration transducer 200 is a piezoelectric transducer. The sensing area 205 is an area in which fluid to be sensed is located. In operation, the concentration transducer 200 generates ultrasonic sound 203, which propagates through the fluid located within the sensing area 205 toward the target 210. The ultrasonic sound 203 (or a portion of it) generated by the concentration transducer 200 reflects off the target 210 and travels back toward the concentration transducer 200 as an echo 207. The time it takes for the ultrasonic sound 203 to travel from the concentration transducer 200 to the target 210 and return to the concentration transducer 200 is referred to as a concentration time-of-flight (ToF). Since the distance between the concentration transducer 200 and the target is known and the time between the excitation of the concentration transducer 200 via an electric signal (and the associated generation of the ultrasonic sound 203) and the subsequent excitation of the transducer via the echo 207 of the ultrasonic sound 203 can be measured, for example, via an electronic processor described below, it is possible to determine the speed of the sound in the fluid.

The level sensor 175 senses a level, and thus a quantity, of the fluid. In the illustrated example, the level sensor 175 includes a level transducer 215 (for example, a piezoelectric transducer), a level sensing tube 220 (for example, a level focus tube), and a level sensing receiving tube 221 configured to receive the level sensing tube 220. The level transducer 215 operates in a similar manner as the concentration sensor in the sense that it generates an ultrasonic sound 203 in response to an electric signal and outputs an electric signal in response to receiving an echo. However, there is no target in the level sensor 175. Instead, an echo is produced when an ultrasonic sound generated by the level transducer interacts with the air-fluid interface in the tank at the “top” of the fluid, for example level 109 (described below). The level ToF signal generated as a result is used by the sensor control system to determine a level or height. If other dimensions of the tank are known, a volume may be determined. For example, in a simple rectangular tank, volume=sensed height (or level)*width (known)*length (known). The level sensing tube 220 acts as a sensing area for containing a fluid to be sensed. In some instances, level sensor 175 includes a float instead of or in addition to the level transducer 215. In the one example, the level sensor 175 includes a float 225 located within the level sensing tube 220. Although illustrated as a sphere in FIG. 3B, the float 225 may be another shape, for example, a cylinder. The float 225 floats on the surface of the fluid. The float 225 includes or is connected to other elements that generate a signal that is representative of the height of the float as it moves in correlation to the surface of the fluid.

Figure 8:
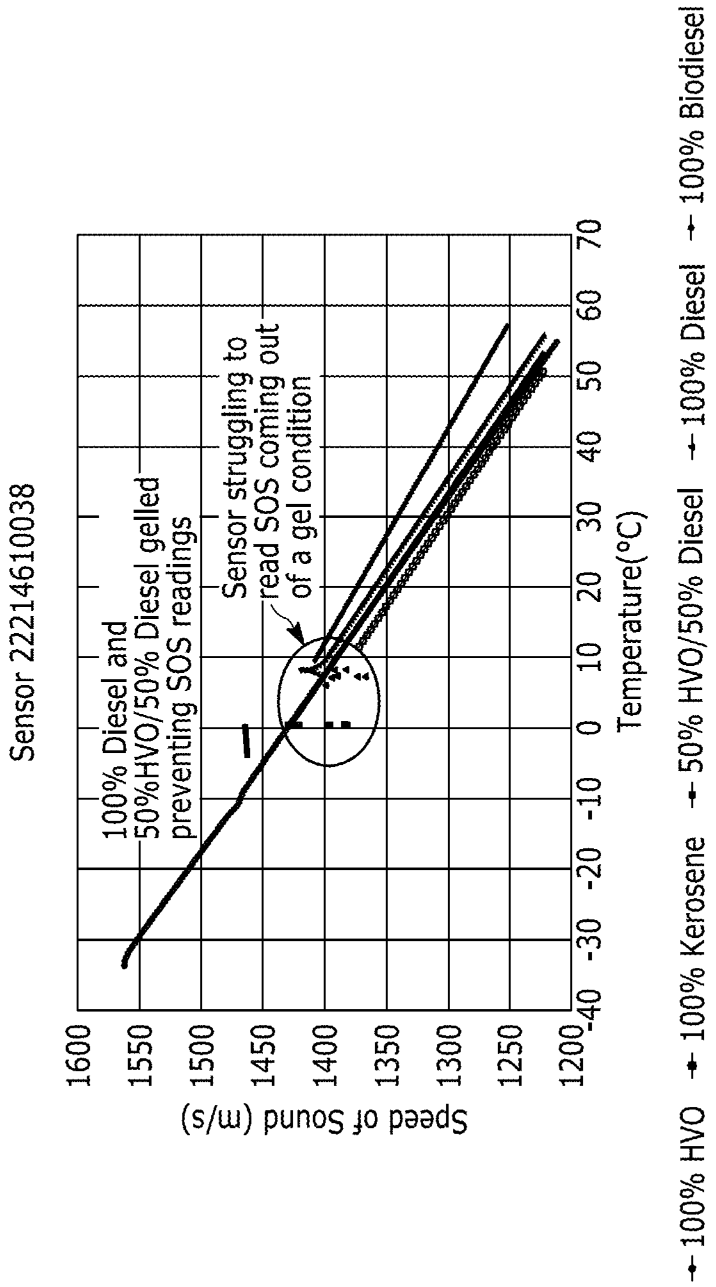
FIG. 8 is a graph of the speed of sound through different types of fluid at various temperatures.

The speed of sound through a fluid may also be affected by temperature, for example, as shown in FIG. 8. Thus, in some instances, temperature is used in a number of the determinations made by the sensor control system. The temperature sensor 180 senses a temperature of the fluid (or outputs a signal representative of the temperature) used by the sensor control system. In one example, the temperature sensor 180 is a thermocouple. In another example, the temperature sensor 180 is a thermistor. In yet another example, the temperature sensor 180 is a resistance temperature sensor. In yet another example, the temperature sensor 180 is an infrared temperature sensor. In instances where the fluid sensor 100 is used in an environment with a relatively constant temperature, it is not necessary to measure the temperature of the fluid.

The capacitor 190 is a capacitance sensing element for sensing a capacitance of the fluid (or outputting a signal indicative of capacitance). As described later, the sensed capacitance is used to determine a dielectric constant. In the example shown, the capacitor 190 is positioned adjacent to the sensing area 205 in a manner that avoids interference with the ultrasonic sound 203 traveling between the concentration transducer 200 and the target 210. In another example, the capacitor 190 includes a first parallel plate 192 and a second parallel plate 194 separated by a distance. The capacitor has a top 193. The fluid in the tanks flows between the first parallel plate 192 and second parallel plate 194 and acts as a dielectric. In some examples, this distance is 1 mm. In other examples the distance between the first parallel plate 192 and the second parallel plate 194 may range from 0.5 mm to 2 mm.

In some instances, the capacitor 190 is also configured to sense the level of the fluid below a fluid level threshold 195. In some examples, the top 193 of the capacitor 190 is configured to be the same height as a concentration transducer housing 196 surrounding the concentration sensor 170 and the fluid level threshold 195. In some examples, if the fluid level is below the fluid level threshold 195, the capacitor 190 measures the level of the fluid. The height of the fluid level threshold 195 is dependent on a minimum ToF of the ultrasonic sound 203 generated by level transducer 215 that will allow the level transducer 215 to collect a reading. It should be understood, a minimum ToF is affected by ringing of a piezoelectric transducer, including for example, the level transducer 215. As noted above, a piezoelectric transducer is excited by an electric signal (usually an electric pulse or pulse train). When the excitation ends, the transducer will not immediately stop moving. Instead, the transducer will continue to vibrate or ring for a certain period. If an echo is received by the transducer while it is still ringing, the echo will not be sensed (or at least sensed correctly). In other words, it is difficult or impossible to collect a reading. Thus, when the level of the fluid in the tank is low, it is possible that an echo could be received before the transducer stops ringing. To help avoid this situation, the fluid level threshold 195 can be set as the level at which the ToF is sufficiently long to ensure that an echo is received after ringing stops. In some examples, the fluid level threshold 195 is at a first distance D1 away from the level read face 217. The amount and duration of ringing is dependent on the construction of the transducer and is often provided by transducer manufacturers. In some examples, the height of the fluid level threshold is 20 mm measured from the level read face 217. In some examples, the height of the fluid level threshold is between 15 mm and 40 mm measured from the level read face 217.

FIG. 3A also illustrates a second distance D2 and a third distance D3. The second distance D2 is the distance from the level read face 217 of the level transducer 215 to a bottom face 198 of the sensor 100. In some examples, the second distance D2 is 15 mm. The third distance D3 is the distance from the bottom face 198 of the sensor 100 and a bottom 107 of the tank 105. In some examples, the third distance D3 is dependent on the depth of the tank 105. In some examples, the sum of D2 and D3 is an Offset, which will be further described below.

In some examples, a protective coating 201 is applied to the bottom face 198 of the sensor 100. In the example shown, a connector cable 199 extends from the PCB 165 to electrical components external to the sensor 100. In some examples, the connector cable 199 extends from the PCB 165 to an external controller 340.

Figure 4A:
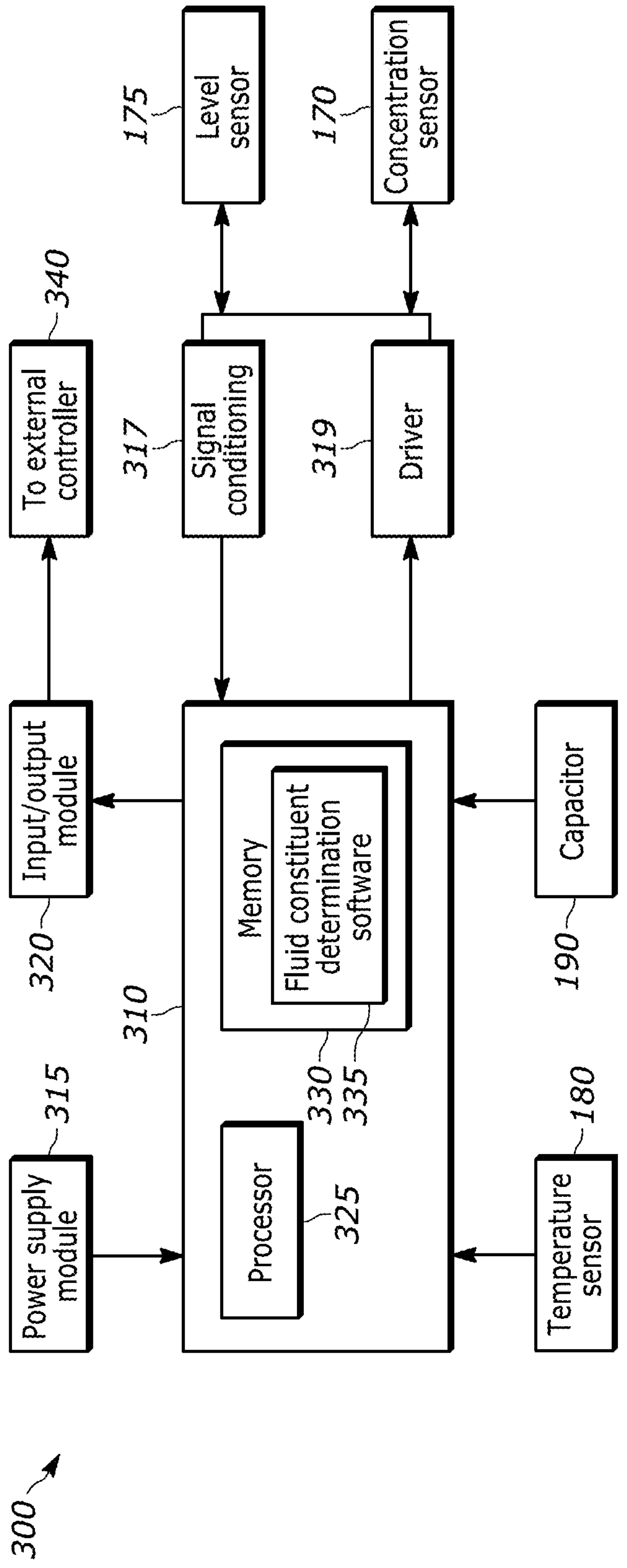
FIG. 4A is a block diagram of a control system of the fluid sensor or sensing system of FIG. 1, according to some examples.

FIG. 4A is a block diagram of a control system 300 of the fluid sensor 100. In one example, the control system 300 is configured to determine a percentage of two or more constituent components of the fluid (for example, diesel, kerosene, and biodiesel) based on the speed of sound, the capacitance, and a relationship in which the sum of the percentages of the two or more constituent components of the fluid is equal to one hundred.

In one example, determinations are made using a system of equations, as follows:

$$PD+PK+PB=100\text{ percent} \tag{1}$$

$$PD*CD+PK*CK+PB*CB=Cf \tag{2}$$

$$PD*SOSD+PK*SOSK+PB*SOSB=SOSf \tag{3}$$

In these equations, the constituent components of the fluid are diesel (D), kerosene (K), and biodiesel (B). SOS denotes speed of sound and C denotes capacitance. PD denotes the percentage of diesel, PK denotes the percentage of kerosene, and PB denotes the percentage of biodiesel. CD denotes the capacitance of diesel, CK denotes the capacitance of kerosene, and CB denotes the capacitance of biodiesel. Cf denotes the (total) capacitance of the fluid being sensed. SOSD denotes the speed of sound of diesel, SOSK denotes the speed of sound of kerosene, and SOSB denotes the speed of sound of biodiesel. SOSf denotes the (total) speed of sound of the fluid being sensed. It should be understood that percentages are typically expressed as a number or ratio that represents a fraction of 100. However, percentages may be expressed in decimals such that the sum of the percentages is equal to 1. Thus, the system of equations above may be modified for decimal calculations.

In one instance, the controller 310 first determines the temperature of the fluid, for example based on a signal from the temperature sensor 180. The controller 310 then determines, for example, using a lookup table that includes known speed of sound values for the constituent components at various temperatures, the speed of sound of diesel (SOSD), the speed of sound of kerosene (SOSK), and the speed of sound of biodiesel (SOSB).

As noted, in some examples, the control system 300 includes a speed of sound look-up table containing SOSD, SOSK, and SOSB values corresponding to a speed of sound value for a given temperature, for example, speed of sound values for temperatures ranging from −50 to 150 degrees Celsius. In other instances, a database or similar mechanism stored in the memory 330 may be used. Similarly, a capacitance look-up table, database, or similar mechanism may be stored in the memory 330 containing CD, CK, and CB values corresponding to a measured value of temperature. For example, the look-up table may include capacitance values for temperatures ranging from −50 to 150 degrees Celsius.

Once the SOSD, SOSK, and SOSB and CD, CK, and CB are determined, the values are used in the systems of equations noted above, given that Cf and SOSf can be measured or sensed by the fluid sensor 100.

In other examples, the memory 330 may contain a look-up table for each constituent component of the fluid. For example, the memory 330 may contain a look-up table of diesel concentrations, kerosene concentrations, and biodiesel concentrations. In some examples, the inputs to the look-up tables are the temperature of the fluid, the speed of sound through the fluid, and the capacitance of the fluid and the outputs are the concentrations of the constituent components of the fluid. In some instances, the look-up table is a three-index look-up table.

FIG. 8 is a graph of the speed of sound of different types of fluid versus temperature.

The speed of sound, at a given temperature, through the fluid can be expressed by the relationship:

$$\text{Speed of sound }(T)=d\times N\times 2/T \tag{1}$$

where d is the distance between the transducer and the reflector (referred to as Dt above), T is the time measurement for multiple echo reflection, and N is the number of reflections or echoes. In some examples, the control system 300 calculates the temperature-dependent speed of sound for the ultrasonic wave traveling through the fluid using this relationship. In some examples, the Speed of Sound (T) is SOSf.

Figure 9:
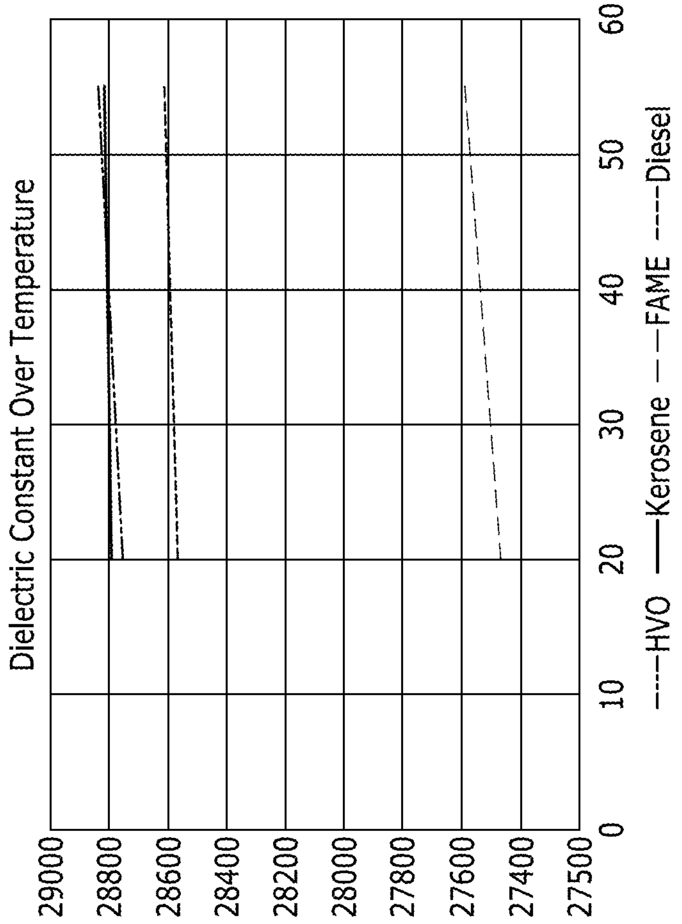
FIG. 9 is a graph of the dielectric constant of different types of fluid at various temperatures.

In some examples, the control system 300 is also configured to calculate the dielectric constant of the of the fluid. In some examples, the dielectric constant of the fluid is calculated using the following equation:

$$k=(\varepsilon_0*(A/d))/C \tag{1}$$

where k represents the dielectric constant of the fluid, $\varepsilon_0$ represents the permittivity of free space, A is the total area of the parallel plates 192 and 194 of the capacitor 190, d is the distance between the first parallel plate and the second parallel plate of the capacitor 190, and C is the capacitance of the fluid determined by control system 300 based on information or a signal provided by the capacitor 190. In some examples, the capacitance is temperature dependent. FIG. 7 is a table of physical properties of example types of constituent components of the fluid. The table includes physical properties for diesel, kerosene, and two types of biodiesels (FAME and HVO), including dielectric constants. Certain examples described herein are designed to work in instances where there are three constituent components, for example, diesel, kerosene, and a single type of biodiesel. FIG. 9 includes a graph of dielectric constants versus temperature for different types of diesels, kerosene, HVO, and FAME.

In some examples, the determination of the dielectric constant is used as an indicator of the presence of water in the fluid. In other words, it is possible to determine or detect the presence of water. The dielectric constant of diesel fuel is approximately 4 while the dielectric constant of water is greater than 70. Water is denser than diesel fuel, which causes it to settle at the bottom 107 of the tank 105 (for example, see FIG. 2) and close to the location of the capacitor 190. The difference in densities between diesel fuel and water is utilized in by the control system 300. In some instances, the control system 300 is configured to determine the presence of water in the tank 105 using the calculated dielectric constant based on the capacitance measurements from the capacitor 190. In some examples, if the dielectric constant determined by the control system 300 is greater than 5, the control system 300 assumes that there is water present in the tank 105.

In some examples, the control system 300 is also configured to determine the level 109 of the fluid in the tank 105. In the level sensor 175, the physical distance between the level transducer 215 and the level 109 of the fluid can be calculated based on the known speed of sound for the fluid and any mechanical offset that may exist between the level transducer 215 and the bottom of the tank 105 as expressed by the relationship:

$$\text{Level} = \text{Offset} + \text{Speed of Sound } (t) \times T/2 \qquad (1)$$

where Offset is the mechanical offset between the bottom 107 of the tank 105 and the level read face 217, Speed of Sound (t) is the temperature-dependent speed of sound for the fluid, and T is the time measurement for the validated echo reflection.

In some examples, components of the control system 300, apart from the sensors, are mounted on the PCB 165 of the fluid sensor 100. In some examples, the control system 300 includes a plurality of electrical and electronic components that provide power, operation control, and protection to the components and modules within the control system 300 and/or the fluid sensor 100. For example, the control system 300 includes, among other things, a controller 310, a power supply module 315, and an input/output module 320. The controller 310 includes, among other things, an electronic processor 325 (such as a programmable microprocessor, microcontroller, or similar device) and a memory 330. The electronic processor 325 is electrically connected to the memory 330 and, in some instances, executes instructions stored in the memory 330 related to the control processes and methods described herein. In one instance, those instructions include fluid constituent determination software 335 architected to determine constituent components of the fluid in accordance with the teachings herein. In other examples, the control system 300 includes additional, fewer, or different components.

The power supply module 315 supplies a nominal voltage to the control system 300 or other components of the fluid sensor 100. In one example, the power supply module 315 supplies a nominal DC voltage. The power supply module 315 is powered by a power source having a nominal voltage and is configured to supply lower voltages to operate circuits and components within the control system 300 or fluid sensor 100.

In some examples, the control system 300 includes a signal conditioning circuit 317 and a driver 319. In some examples, one or more of the signal conditioning circuit 317 and the driver 319 may be included in the controller 310. The signal conditioning circuit 317 serves to amplify and filter a low-level signal received from the concentration sensor 170 in response to being stimulated by a received echo 207 of the ultrasonic sound 203. In one example, the controller 310 sends a series of drive pulses and a drive pulse amplitude command signal to the driver 319. In some examples, the drive pulses are at the resonant frequency of the concentration transducer 200. The driver 319 amplifies the signal, applying a series of higher voltage pulses to the concentration transducer 200, causing the concentration transducer 200 to emit the ultrasonic sound 203. In some examples, the signal conditioning circuit 317 and the driver 319 are also connected to the level sensor 175.

The input/output module 320 transmits data from the control system 300 to an external controller 340. The input/output module 320 also receives data from the external controller 340. When the fluid sensor 100 is in normal operation, it operates in a measurement mode, in which it transmits data to the external controller 340 indicative of the measured and determined fluid characteristics. The external controller 340 may be, for example, an electronic control unit (ECU) located on a diesel-powered vehicle. The external controller 340 may be linked through a communication module on a vehicle's communication bus (for example, a CAN bus). In some examples, the input/output module 320 communicates by means of a protocol such as J1939 or CAN bus for communicating directly to the external controller 340. In other examples, the input/output module 320 communicates under other suitable protocols, including analog or digital signals, depending on the needs of the specific application. In some examples, the input/output module 320 communicates by means of a pulse-width modulated signal.

Although in one example, the control system 300 is shown mounted on the PCB 165, it should be understood that all or part of the processing performed by the control system could be distributed and performed on one or more electronic processors or including processors not located on the PCB 165, for example, one or more electronic processors in or connected to a vehicle in which the sensor 100 is installed.

Figure 4B:
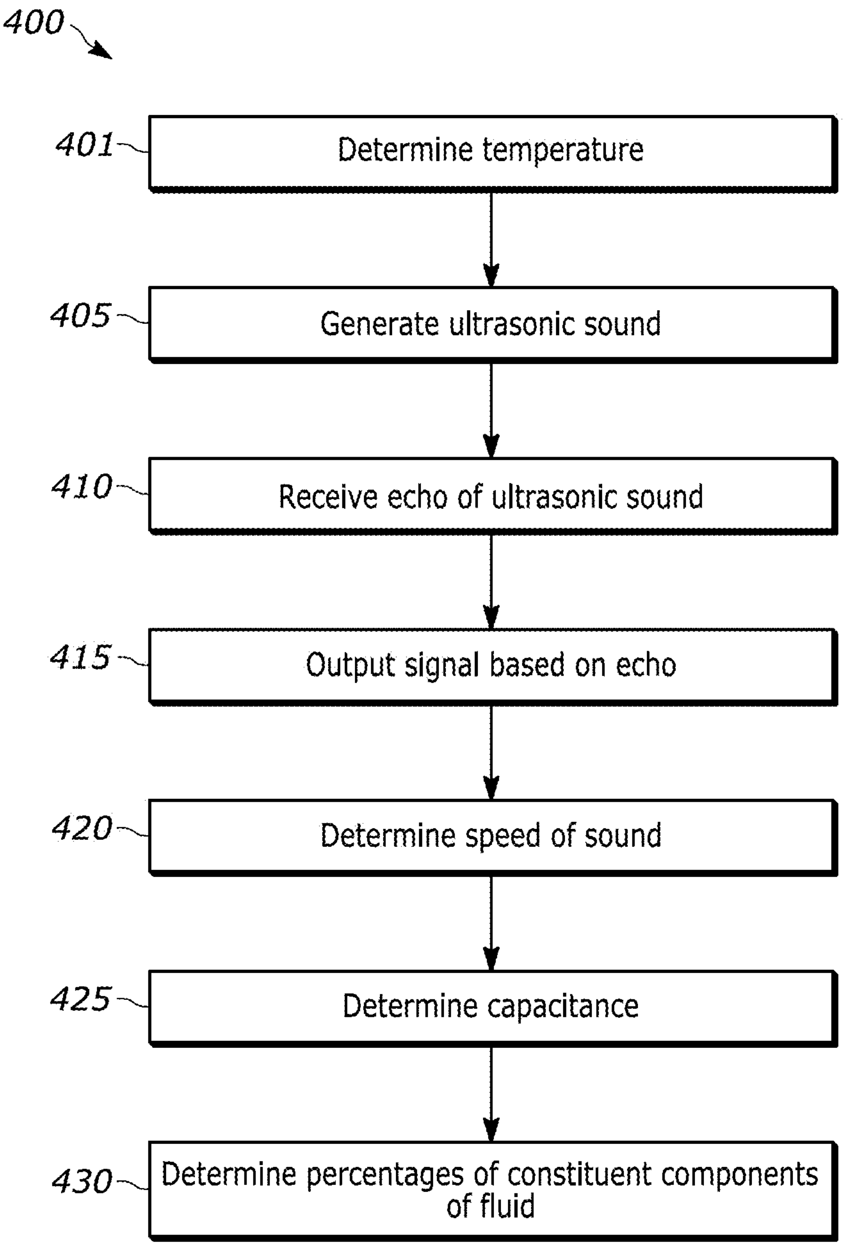
FIG. 4B is a flow chart illustrating a method of determining a percentage of each of two or more constituent components of a fluid, according to some examples.

FIG. 4B illustrates one example of a method 400 for determining a percentage of each of two or more constituent components of a fluid. Examples herein describe methods for determining a percentage of three constituent components of a fluid. However, it is possible to the determine the percentage of more than three constituent components if additional relationships are available. For example, it is possible to determine a fourth property or constituent component of the fluid if a system of four equations is available.

In the text that follows, it is assumed that the method 400 is performed with the fluid sensor 100 when submerged in fluid. In step 401, the temperature of the fluid is determined. In step 405, the concentration transducer 200 transmits an ultrasonic wave to the target 210. The concentration transducer 200 receives the echo 207 of ultrasonic sound 203 reflected from the target 210 (step 410). The controller 310 receives a signal from the concentration transducer 200 that indicates when the echo 207 of the ultrasonic sound 203 is received. Based on the received signal, the controller 310 calculates the ToF of the ultrasonic sound 203 based on a time difference between when the ultrasonic sound 203 was generated and when the echo 207 ultrasonic sound 203 was received. The controller 310 outputs a signal based on the time of flight of the ultrasonic sound 203 (step 415). The controller 310 determines a speed of sound through the fluid based on the output signal (step 420). In some examples, the speed of sound through the fluid is determined using the speed of sound determination technique described above.

The controller 310 also receives a signal from the capacitor 190 that indicates the capacitance of the fluid between the first parallel plate 192 and the second parallel plate 194. Based on the received signal, the controller 310 determines the capacitance of the fluid (step 425). With the determined speed of sound through the fluid and the capacitance of the fluid, the controller 310 determines the percentages of each of two or more constituent components of the fluid (step 430). In some examples, the percentages of each of two or more constituent components of the fluid are determined using the technique described above.

Figure 5:
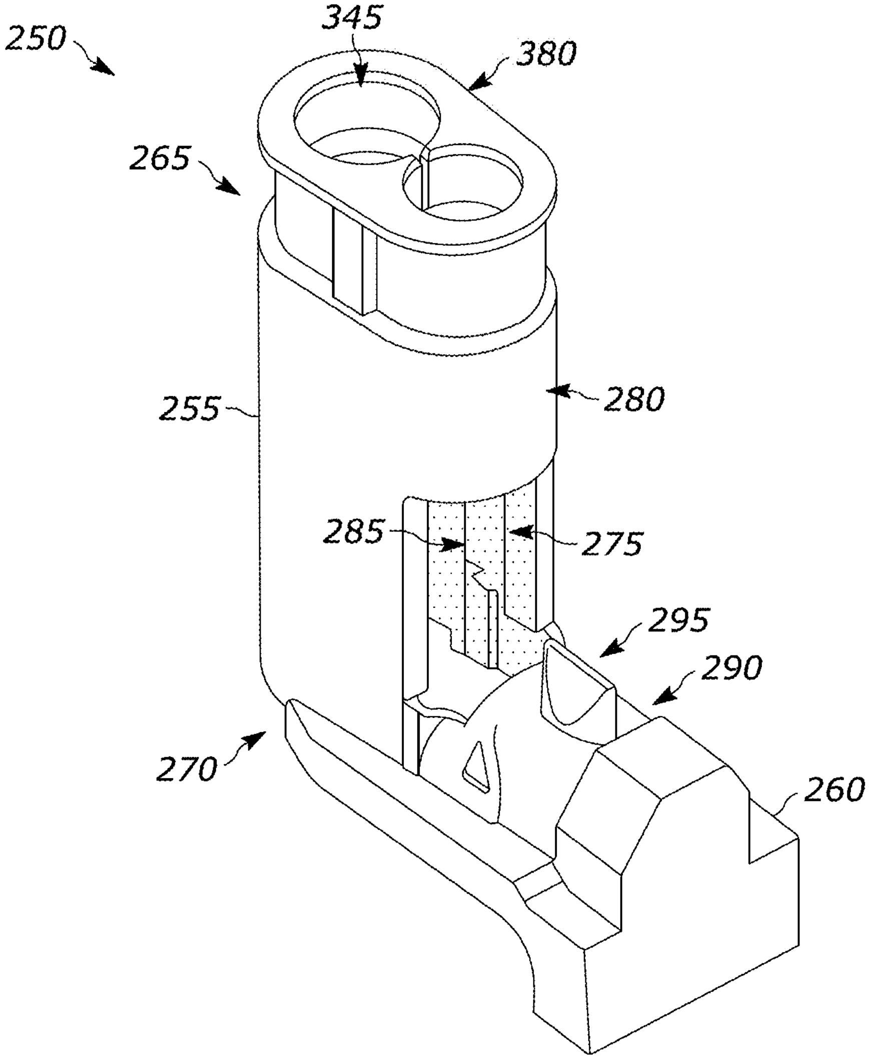
FIG. 5 is a top perspective view of an aeration filter, according to some examples.

Fluid in the tank 105 may become aerated and when so aerated may have a liquid portion and a gas portion. In some examples, the gas portion includes bubbles of air, or another gas, present in the fluid as a result, for example, from sloshing in a tank that mixes air in the fluid. FIG. 5 illustrates a boot or aeration filter 250 that helps prevent gas bubbles from entering the sensing areas, including the sensing area 205. The aerations filter helps to prohibit, or inhibit, a flow of bubbles (i.e., air or other gas trapped in liquid) into the sensing area. The aeration filter 250 overlays the top 131 of the sensing system 130. The aeration filter 250 may be made from rubber or a similar pliable material. In the illustrated example, the aeration filter 250 is substantially "L" shaped having a main body 255 and a leg 260. The main body 255 has a top 265 and a bottom 270. The leg 260 is coupled to the main body 255 at the bottom 270. The aeration filter 250 also has an interior 275 and an exterior 280.

In some instances, the aeration filter 250 also includes a chimney 290 having a vent 295. The chimney 290 is configured to exhaust an entrapped gas portion (i.e., entrapped gas bubbles) from the one or more sensing areas. Because the entrapped gas portion is less dense than the liquid and because of convection the gas portion flows out of the one or more sensing areas through the chimney 290. Once the gas portion has exited the sensing areas, the gas portion is free to escape up through the fluid to a surface of the fluid.

In the example illustrated in FIG. 5, the aeration filter 250 also includes a port or receptacle 380. In the example shown, the receptacle 380 is a dual-opening port configured to receive the level sensing tube 220 and couples the level sensing tube 220 to the level sensing receiving tube 221 of the sensing system 130. In some examples, the receptacle 380 includes a plurality of striations (for example, ridges) 345 configured to promote coupling of the bottom of the level sensing tube 220 to the level sensing receiving tube 221 of the sensing system 130.

In the example illustrated in FIG. 5, the aeration filter 250 also includes a retainer. The retainer is configured to hold the aeration filter 250 onto the sensing system 130. The retainer may include a toe clip 350. The toe clip 350 is configured to capture a toe 355 of the sensing system 130 to retain the aeration filter 250 onto the sensing system 130.

Figure 6:
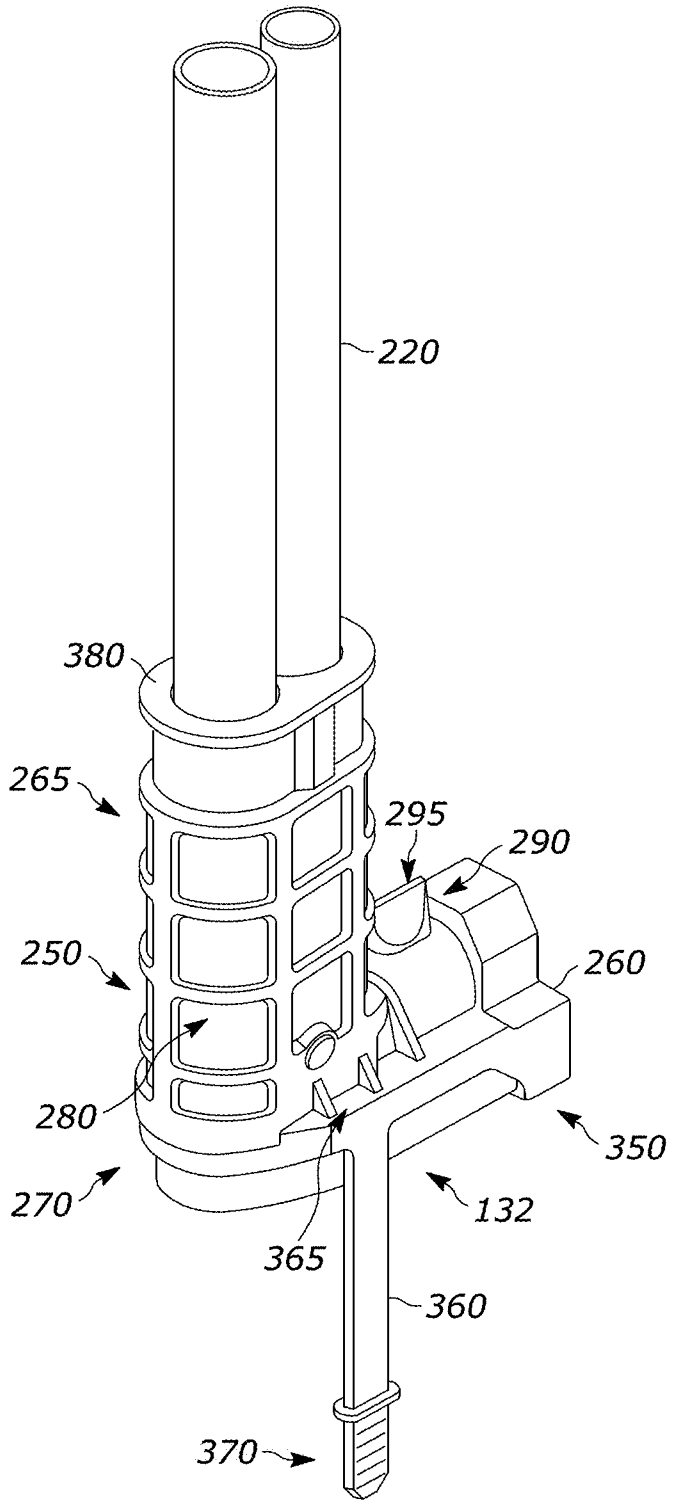
FIG. 6 is a perspective view of the aeration filter of FIG. 5 positioned on the sensor or sensing system of FIG. 3A or FIG. 3B, according to some examples.

As illustrated in FIG. 6, the retainer may also include a strap 360. The strap 360 extends from a first side 365 of the aeration filter 250, wraps around a bottom 132 of the sensing system 130, and releasably attaches to a second side, opposite the first side of the aeration filter 250. In the illustrated example, the strap 360 includes a buckle 370 for releasably attaching the strap 360 to the second side of the aeration filter 250.

Referring now back to additional features illustrated in FIGS. 1 and 2, in some instances, the fluid sensor 100 is part of a larger assembly with components that facilitate installation and location within a tank 105.

The fluid sensor 100 may include a header 110, a pickup line 120, a return line 125. The header 110 is configured to be coupled to the tank 105, for example, via threads. In some examples, a gasket 135 seals the header 110 to the tank 105. The header 110 includes a plurality of fittings and an electrical connector 140. In some examples, the plurality of fittings includes a pickup fitting 145 and a return fitting 150. The plurality of fittings provides various paths for fluid to be transported or directed into, out of, and through the tank 105. The electrical connector 140 provides an electrical connection from the sensing system 130 to an external computer system (for example, to the external controller 340 via a vehicle's data bus).

As noted above, the sensor 100 may be implemented and configured in several different ways. In some instances, the sensor 100 is configured to determine a dielectric constant without determining the percentages of the constituent components of the fluid. In one such example, the sensor 100 includes a target; a temperature sensor; and a transducer positioned opposite the target at a fixed, predetermined distance from the target. The transducer is configured to generate an ultrasonic sound, receive an echo of the ultrasonic sound, and output a signal based on the echo. The sensor 100 also includes a sensing area located between the transducer and the target; and a capacitor including a first parallel plate and a second parallel plate separated by a distance. The sensor 100 also includes an electronic processor electrically connected to the temperature sensor, the transducer, and to the capacitor and configured to determine a dielectric constant of the fluid based on a signal from the temperature sensor, a signal from the capacitor, and a signal from the transducer. In some instances, the electronic processor determines a speed of sound of a fluid based on the signal from the transducer and determines a capacitance of the fluid based on a signal from the capacitor. This example may be modified or combined with other features and aspects described herein.

In different example, the sensor 100 includes a target; a temperature sensor; and a transducer positioned opposite the target at a fixed, predetermined distance from the target. The transducer is configured to generate an ultrasonic sound, receive an echo of the ultrasonic sound, and output a signal based on the echo. A sensing area is located between the transducer and the target. The sensor 100 also includes a capacitor. The sensor includes an electronic processor electrically connected to the temperature sensor, the transducer, and to the capacitor. The electronic processor is configured to determine a temperature of the fluid based on a signal from the temperature sensor, determine a speed of sound of a fluid based on the signal from the transducer, determine a capacitance of the fluid based on a signal from the capacitor, and determine a percentage of a number of constituent components of the fluid using a system of equations that includes a number of equations that equals or exceeds the number of constituent components of the fluid.

Thus, examples described herein provide, among other things, mechanisms and techniques for sensing and calculating various physical properties of a fluid. Various features and advantages are set forth in the following claims.

What is claimed is:

1. A fluid sensor comprising:

a target;

a transducer positioned opposite the target at a fixed, predetermined distance from the target and configured to generate an ultrasonic sound, receive an echo of the ultrasonic sound, and output a signal based on the echo;
a sensing area located between the transducer and the target;
a capacitor; and
an electronic processor electrically connected to the transducer and to the capacitor and configured to:
determine a speed of sound of a fluid based on the signal from the transducer;
determine a capacitance of the fluid based on a signal from the capacitor; and
determine a percentage of each of two or more constituent components of the fluid based on the speed of sound, the capacitance, and a relationship in which a sum of the percentages of the two or more constituent components equals one hundred.

2. The fluid sensor of claim 1, further comprising a temperature sensor electrically connected to the electronic processor.

3. The fluid sensor of claim 1, wherein the capacitor is positioned adjacent the sensing area.

4. The fluid sensor of claim 3, wherein the capacitor is configured to sense a level of the fluid below a fluid level threshold.

5. The fluid sensor of claim 4, wherein a height of the capacitor is equal to the fluid level threshold.

6. The fluid sensor of claim 5, wherein the fluid level threshold is between 15 mm and 40 mm.

7. The fluid sensor of claim 1, wherein the capacitor comprises a first parallel plate and a second parallel plate separated by a distance between 0.5 mm and 2 mm.

8. The fluid sensor of claim 1, wherein the two or more constituent components include diesel, kerosene, and biodiesel.

9. The fluid sensor of claim 1, wherein the electronic processor is further configured to determine a dielectric constant of the fluid.

10. The fluid sensor of claim 9, wherein a presence of water in the fluid is determined based on the dielectric constant of the fluid.

11. The fluid sensor of claim 10, wherein the presence of water in the fluid is determined when the dielectric constant of the fluid is greater than 5.

12. The fluid sensor of claim 1, further comprising a level sensor electrically connected to the electronic processor and configured to sense a level of the fluid.

13. The fluid sensor of claim 1, further comprising an aeration filter configured to prevent one or more gas bubbles from entering the sensing area.

14. A method for operating a fluid sensor, the method comprising:
generating, via a transducer, an ultrasonic sound;
receiving an echo of the ultrasonic sound, and outputting, via an electronic processor, a signal based on the echo;
determining, via the electronic processor, a speed of sound of a fluid based on the signal from a transducer;
determining, via the electronic processor, a capacitance of the fluid based on a signal from a capacitor; and
determining, via the electronic processor, a percentage of each of two or more constituent components of the fluid based on the speed of sound, the capacitance, and a relationship in which a sum of the percentages of the two or more constituent components equals one hundred.

15. The method of claim 14, further comprising a determining a temperature of the fluid.

16. The method of claim 14, further comprising sensing a level of the fluid.

17. The method of claim 14, wherein the capacitor is further configured to sense a level of the fluid below a fluid level threshold.

18. The method of claim 17, wherein a height of the capacitor is equal to the fluid level threshold.

19. The method of claim 18, wherein the fluid level threshold is between 15 mm and 40 mm.

20. The method of claim 14, wherein the capacitor comprises a first parallel plate and a second parallel plate separated by a distance between 0.5 mm and 2 mm.

21. The method of claim 14, wherein the two or more constituent components includes diesel, kerosene, and biodiesel.

22. The method of claim 14, further comprising determining a dielectric constant of the fluid.

23. A fluid sensor comprising:
a target;
a temperature sensor;
a transducer positioned opposite the target at a fixed, predetermined distance from the target and configured to generate an ultrasonic sound, receive an echo of the ultrasonic sound, and output a signal based on the echo;
a sensing area located between the transducer and the target;
a capacitor positioned adjacent the sensing area and including a first parallel plate and a second parallel plate separated by a distance; and
an electronic processor electrically connected to the temperature sensor, the transducer, and to the capacitor and configured to:
determine a temperature of the fluid based on a signal from the temperature sensor,
determine a speed of sound of a fluid based on the signal from the transducer,
determine a capacitance of the fluid based on a signal from the capacitor, and
determine a percentage of each of two or more constituent components of the fluid based on the speed of sound, the capacitance, and a relationship in which a sum of the percentages of the two or more constituent components equals one hundred.

* * * * *